United States Patent [19]

Underdown

[11] Patent Number: 5,171,460
[45] Date of Patent: Dec. 15, 1992

[54] METHOD FOR PREVENTING METAL CARBONATE SCALE FORMATION IN A WELL PENETRATING A SUBTERRANEAN FORMATION

[75] Inventor: David R. Underdown, Plano, Tex.

[73] Assignee: Atlantic Richfield Company, Los Angeles, Calif.

[21] Appl. No.: 706,685

[22] Filed: May 29, 1991

[51] Int. Cl.$^5$ .................. C02B 5/06; E21B 43/00
[52] U.S. Cl. .................. 252/8.552; 252/8.555; 252/180; 166/311; 166/312; 507/90; 507/128
[58] Field of Search .................. 166/311, 312; 252/8.552, 8.555, 180; 507/90, 128

[56] References Cited

U.S. PATENT DOCUMENTS

| | | | |
|---|---|---|---|
| 3,336,221 | 8/1967 | Ralston | 252/8.552 X |
| 3,481,869 | 12/1969 | Jones | 252/8.552 X |
| 3,483,925 | 12/1969 | Slyker | 166/279 |
| 3,668,137 | 6/1972 | Gardner | 252/8.555 X |
| 3,867,286 | 2/1975 | Quinlan | 252/180 |
| 3,958,635 | 5/1976 | Zilch et al. | 252/180 X |
| 3,966,630 | 6/1976 | Quinlan | 252/8.552 |
| 4,080,375 | 3/1978 | Quinlan | 252/8.554 |
| 4,088,574 | 5/1978 | Quinlan | 252/8.554 X |
| 4,493,771 | 1/1985 | Wilson et al. | 252/180 X |
| 4,857,205 | 8/1989 | Redmore et al. | 166/279 X |
| 4,931,189 | 6/1990 | Dhawan et al. | 252/180 X |
| 5,019,343 | 5/1991 | Hwa et al. | 252/8.555 X |

Primary Examiner—Robert L. Stoll
Assistant Examiner—C. Sayala
Attorney, Agent, or Firm—F. Lindsey Scott

[57] ABSTRACT

While many materials have been used to inhibit scale formation previously, none have been fully satisfactory to prevent scale formation and precipitation of totally dissolved solids (TDS) in fluids used in well drilling, completion and workovers when the fluids contain divalent metal cations and when the formation contains carbon dioxide. Since many wells are completed into such formations, a continuing search has been directed to an improved method for preventing the formation of such scale. According to the present invention, metal carbonate scale formation and TDS precipitation in a well penetrating a subterranean formation wherein a fluid containing calcium, magnesium, barium or zinc is used in the presence of carbon dioxide is prevented by maintaining the fluid at a pH from about 2 to about 9 and adding from about 1 to about 5000 parts per million of a phosphonomethylated oxyalkyleneamine material having a molecular weight from about 150 to about 3000 to the fluid.

13 Claims, 1 Drawing Sheet

METHOD FOR PREVENTING METAL CARBONATE SCALE FORMATION IN A WELL PENETRATING A SUBTERRANEAN FORMATION

FIELD OF THE INVENTION

This invention relates to methods for preventing metal carbonate formation in a well penetrating a subterranean formation wherein a fluid containing a divalent metal cation such as magnesium, barium, calcium or zinc is used in the presence of carbon dioxide.

BACKGROUND OF THE INVENTION

A majority of the oil wells completed in the Gulf of Mexico are completed in formations which contain carbon dioxide gas. Initial completion of these oil and gas wells requires completion fluids in a weight range from about 8.33 pounds per gallon to about 19.2 pounds per gallon to control the well. These fluids often contain divalent metal compounds such as, but not limited to, calcium chloride, magnesium chloride, barium chloride and zinc chloride which result in the presence of divalent metal cations such as calcium, magnesium, barium or zinc in the fluids to obtain the desired weight per gallon. It is well known that if divalent metal cation containing fluids come into contact with carbon dioxide, there is a very strong potential to form divalent metal carbonate solids or scale. In an oil or gas well, the divalent metal carbonate scale frequently occurs in the perforation tunnels or the tubing to the detriment of the production of oil or gas from the well. A common practice for dealing with such scale in oil and gas wells is to acidize the wells with 5 to 10 percent hydrochloric acid after the initial completion. This technique is successful in removing the scale but involves an additional operation at considerable expense.

U.S. Pat. No. 4,741,400 entitled "Method for Scale Inhibition in a Well Penetrating a Subterranean Formation" issued May 3, 1988 to David R. Underdown; U.S. Pat. No. 4,485,874 entitled "Method for Scale Removal and Scale Inhibition in a Well Penetrating a Subterranean Formation" issued Dec. 4, 1984 to Kevin O. Myers; and U.S. Pat. No. 4,495,996 entitled "Method for Scale Removal and Well Inhibition in a Well Penetrating a Subterranean Formation" issued Jan. 29, 1985 to Kevin O. Myers and Harry L. Skillman, Jr. disclose various processes for removing and controlling scale. An article "Evaluation of Calcium Carbonate Scale Inhibitors for Prudhoe Bay, Alaska" by D. R. Underdown and D. P. Newhouse, SPE 15658 presented at the 61st Annual Technical Conference and Exhibition of the Society of Petroleum Engineers in New Orleans, La. on Oct. 5-8, 1986 also discloses various materials for use as corrosion scale inhibitors.

While many materials have been used to inhibit scale formation previously, none have been fully satisfactory to prevent scale formation in fluids used in well drilling, completion and workovers when the fluids contain calcium, magnesium, barium or zinc cations and when the formation contains carbon dioxide. Since many wells are completed into such formations, a continuing search has been directed to an improved method for preventing the formation of such scale.

SUMMARY OF THE INVENTION

According to the present invention, divalent metal carbonate scale formation in a well penetrating a subterranean formation wherein a fluid containing calcium, magnesium, barium or zinc is used in the presence of carbon dioxide is prevented by maintaining the fluid at a pH from about 2 to about 9 and adding from about 1 to about 5000 parts per million of a phosphonomethylated oxyalkyleneamine having a molecular weight from about 150 to about 3000 to the fluid.

DESCRIPTION OF PREFERRED EMBODIMENTS

Figures 1, 2:
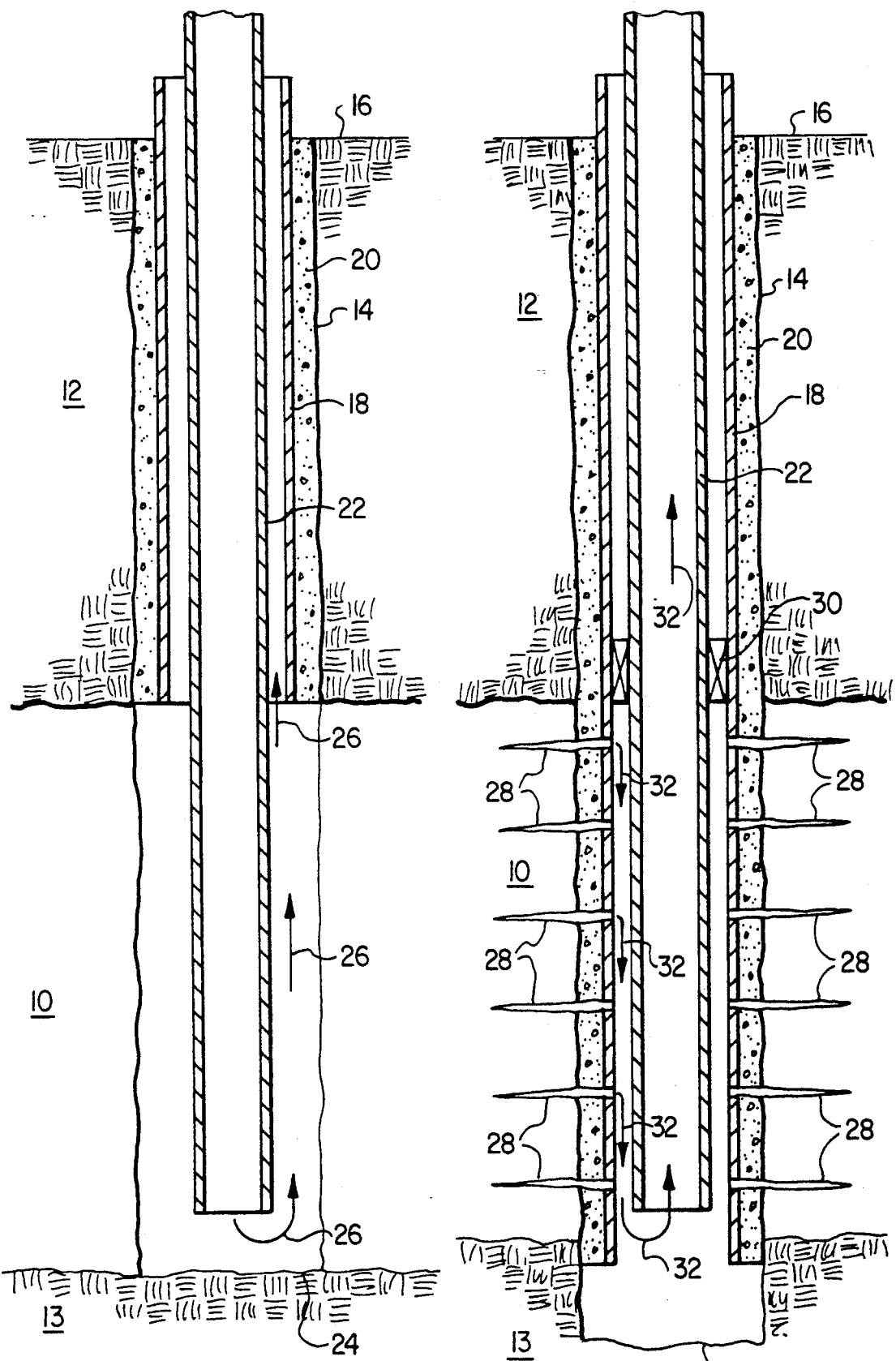
FIG. 1 is a schematic diagram of a well which has been drilled to total depth penetrating a subterranean formation.
FIG. 2 is a schematic diagram of a well which has been drilled through and cased through a subterranean formation of interest and completed for the production of fluids from the formation of interest.

The same numbers will be used throughout the following discussion of the Figures to refer to the same or similar components.

In FIG. 1, a formation of interest 10 beneath an overburden 12 and above an underlying formation 13 is penetrated by a well 14 from the surface 16. A casing 18 has been positioned in well 14 to the top of formation 10 and cemented in place with cement 20. A tubing 22 is positioned in well 14 extending to near the bottom 24 of well 14. Tubing 22 could also be a drillstring with a drill positioned on the lower end of the drillstring to continue to drill well 14 to a greater depth. Similarly, tubing 22 can be used to clean out the well or the like. Tubing 22 can also be used for production of fluids from formation 10 if desired. In such instances, a packer or the like would generally be positioned to prevent flow of fluids up the annulus between tubing 22 and casing 18. In general, when fluids are circulated through the well, the fluid is circulated down tubing 22, out the bottom of tubing 22 and upward through the annulus between casing 18 and tubing 22 as shown by arrows 26. A variety of drilling and completion activities are completed in this fashion. Frequently packers and the like are used to control the placement of materials, the flow of fluids and the like. The fluids used are of a density selected for control of the well and generally contain calcium, zinc, barium, magnesium or other metal constituents as necessary to vary the density of the fluids for well control.

In FIG. 2, a well which has been completed for production from formation 10 is shown. In FIG. 2, well 14 has been cased to the bottom of formation 10 and flow through the annulus between tubing 22 and casing 18 is blocked by a packer 30. The well has been completed for production from formation 10 by completion of a series of perforations 28 which permit fluid communication from formation 10 through casing 18 so that production can be accomplished from tubing 22 as shown by arrows 32. Unless fluids will flow up tubing 22 by pressure from formation 10, a pump (not shown) may be used to pump fluids up tubing 22 as known to those skilled in the art.

A large number of variations are possible in drilling, completion and working over of wells. Generally, drilling operations refer to those operations involved with completing the well to its total depth with or without casing in the well to some portion of its total depth. Completion operations refer to operations which may include cementing at least a portion of the casing in place. perforating the well, positioning packers and other means necessary for the accomplishment of the desired flows, perforating the casing, if necessary, and the like. It will be understood that some wells may be produced open hole and will not be cased to total depth. Workover operations refer to operations conducted after the beginning of production to improve production rates or the like. Such operations could include re-perforation, acidizing, fracturing and the like. All such operations use fluids which are of an adjusted weight per gallon to control the well during the operation. These fluids, which typically contain divalent cations, have the potential to form divalent metal carbonate scale in the presence of carbon dioxide in the wellbore, in the tubing, in the perforations and in portions of the formation near the well which are contacted by the fluids.

Such fluids typically contain metals such as calcium, zinc, barium, magnesium and the like frequently in the form of halides but by no means always in this form. The problem results from the presence of the divalent metal ions in the fluid which is usually aqueous in the presence of carbon dioxide. As the fluid circulates through the well, the presence of carbon dioxide tends to result in the formation of divalent metal carbonates. These carbonates tend to precipitate or simply form on the nearest surface. Surfaces which are particularly vulnerable are surfaces such as perforations and openings from formation 10 where carbon dioxide flows into the wellbore. At this point of contact between carbon dioxide and the divalent metal ion-containing fluid, scale tends to form and plug off the small openings. Such is very detrimental to the production of fluids from formation 10. As indicated previously, the use of acid treatments can remove this scale but such treatments constitute a separate operation and pose some risks of damage to the formation.

According to the present invention, it has been found that the formation of scale in well 14 in the presence of carbon dioxide and such divalent metal ion-containing fluids can be inhibited by maintaining the pH of the fluid from about 2 to about 9 and by adding from about 1 to about 5000 parts per million of phosphonomethylated oxyalkyleneamine (material) having a molecular weight from about 150 to about 3000 to the fluid. Preferably the phosphonomethylated oxyalkyleneamine has a molecular weight from about 200 to about 1000. Such materials have the general formulas:

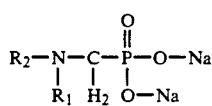     1)

wherein $R_1$ is selected from the group consisting of alkyls containing from 1 to 5 carbon atoms and oxygenated hydrocarbon groups containing from 1 to 10 carbon atoms and wherein $R_2$ is selected from the group consisting of oxygenated hydrocarbon containing groups containing from 1 to 10 carbon atoms;

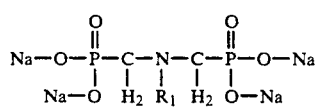     2)

wherein $R_1$ is a defined above; and

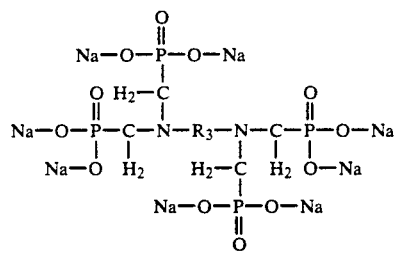     3)

wherein $R_3$ is an alkyl group containing from 1 to 10 carbon atoms or an oxygenated hydrocarbon group containing from 1 to 10 carbon atoms.

Some suitable materials are sodium phosphonate of monoethanolamine, sodium phosphonate of morpholine, sodium phosphonate of bisamine ethyl ether, sodium phosphonate of diglycolamine, sodium phosphonate of N-ethyl diglycolamine and the like.

These materials may be used alone, but are more effective when used in combination. One particularly effective combination is shown below in Table I. Both a suitable and a preferred mixture of materials are shown in Table I.

TABLE I

| Material | Suitable Mixture wt % | Preferred Mixture wt % | Preferred aqueous solution wt % |
|---|---|---|---|
| sodium phosphonate of monoethanolamine | 2.8–7.0 | 4.65 | 1.6 |
| sodium phosphonate of morpholine | 2.8–7.0 | 4.65 | 1.6 |
| sodium phosphonate of bisamine ethyl ether | 34–85 | 56.70 | 19.5 |
| sodium phosphonate of diglycolamine | 17–26 | 28.20 | 9.7 |
| sodium phosphonate of N-ethyl diglycolamine | 3.5–8.7 | 5.8 | 2.0 |

The added material is generally added in the form of an aqueous solution which frequently will contain from about 1 to about 5 volume percent methanol, from about 10 to about 20 volume percent ethylene glycol, from about 1 to about 5 volume percent diethylene glycol and from about 20 to about 45 weight percent phosphonomethylated oxyalkyleneamine.

Desirable results have been achieved with the combination shown above when the materials are present in aqueous solution in an amount equal to about 34.4 weight percent. A preferred aqueous solution is shown in Table I.

The materials are effective to prevent scale formation in well fluids containing divalent metal cations in the presence of carbon dioxide and to prevent precipitation of compounds generally referred to as totally dissolved solids (TDS) from the fluids at high divalent metal ion concentrations in the well fluids. Previously phosphonates and polyacrylates have been used for scale inhibition but neither is effective to prevent TDS precipitation in the presence of high divalent metal ion concentrations.

The amount of aqueous solution required to achieve the desired concentration of material in the well fluid can readily be calculated by means known to those skilled in the art and the amount of material required in a particular well fluid to achieve the desired scale inhibition and prevent precipitation of solids in the well fluid can be readily determined by adding the material at an initial concentration and increasing or decreasing the initial rate as necessary until the desired results are achieved with the least material addition. The use of from about 50 to about 1000 ppm of the material will frequently be found suitable for Gulf of Mexico well fluids. While concentrations from about 1 to about 5000 parts per million of the materials in the fluid are considered to be suitable, it is expected that from about 1 to about 2000 parts per million will be effective in most well fluids. Not only is the added material effective in preventing the formation of divalent metal carbonate scale at the small openings entering the wellbore but the material also tends to prevent the precipitation of materials referred to as totally dissolved solids. Use of this material in the fluids used for drilling, completion and workovers results in elimination of the scaling problem in the wellbore, tubing, perforations and in many instances in portions of formation 10 which have been penetrated by the fluids. The material is an effective scale inhibitor when introduced into formation 10. It is not an objective of the present invention per se to introduce the fluid into formation 10 for scale inhibition, but in the event that the fluids do contact formation 10, certain amounts of inhibition should be accomplished in the portions of formation 10 which have been contacted.

The materials in aqueous solution as described in Table I are available as ARCO SB200 from Nalco Chemical Company, P.O. Box 87 Sugar Land, Tex. 77487-0087.

While the fluids may contain materials selected from the group consisting of barium, magnesium, calcium, zinc, and the like, calcium and zinc are used more frequently and are more frequently found as scale. It is considered that formation of divalent metal carbonate scale of any of these metals is inhibited by the use of the present invention.

Having thus described the invention by reference to certain of its preferred embodiments, it is respectfully pointed out that the embodiments described are illustrative rather than limiting and that many variations and modifications are possible within the scope of the present invention. Many such variations and modifications may be considered obvious and desirable by those skilled in the art based upon a review of the foregoing description of preferred embodiments.

What is claimed is:

1. A method for preventing divalent metal carbonate scale formation in a well penetrating a subterranean formation wherein a fluid containing calcium, magnesium, barium or zinc is used in the presence of carbon dioxide in drilling, completion or workover operations, during said drilling, completion or workover operations, said method consisting essentially of:
   (a) maintaining said fluid at a pH from about 2 to about 9; and,
   (b) adding from about 1 to about 5000 parts per million of phosphonomethylated oxyalkyleneamine material having a molecular weight from about 150 to about 3000 to said fluid wherein said material consists essentially of from about 2.8 to about 7.0 weight percent sodium phosphonate of monoethanolamine, from about 2.8 to about 7.0 weight percent sodium phosphonate of morpholine, from about 34 to about 85 weight percent sodium phosphonate of bisamine ethyl ether, from about 17 to about 26 weight percent of sodium phosphonate of diglycolamine and from about 3.5 to about 8.7 weight percent sodium phosphonate of N-ethyl diglycolamine.

2. The method of claim 1 wherein said material is added to said fluid as an aqueous solution containing from about 20 to about 45 weight percent of said material.

3. The method of claim 1 wherein said material is added to said fluid in an amount equal to from about 50 to about 1000 ppm of said material in said fluid.

4. In a method for drilling a well to penetrate a subterranean formation wherein a drilling fluid containing calcium, magnesium, barium or zinc is used in the presence of carbon dioxide during said drilling an improvement comprising
   (a) maintaining said drilling fluid at a pH from about 2 to about 9; and
   (b) adding from about 1 to about 5000 parts per million of a phosphonomethylated oxyalkyleneamine material having a molecular weight form about 150 to about 3000 to said drilling fluid to prevent formation of divalent metal carbonate scale during said drilling wherein said material consists essentially of from about 2.8 to about 7.0 weight percent sodium phosphonate of monoethanolamine, from about 2.8 to about 7.0 weight percent sodium phosphonate of morpholine, from about 34 to about 85 weight percent sodium phosphonate of bisamine ethyl ether, from about 17 to about 26 weight percent of sodium phosphonate of diglycolamine and from about 3.5 to about 8.7 weight percent sodium phosphonate of N-ethyl diglycolamine.

5. The improvement of claim 4 wherein phosphonomethylated oxyalkyleneamine material is added to said drilling fluid as an aqueous solution containing from about 20 to about 45 weight percent of said material.

6. The improvement of claim 4 wherein said phosphonomethylated oxyalkyleneamine is added to said drilling fluid in an mount equal to from about 1 to about 2000 parts per million.

7. The method of claim 4 wherein said material is added to said drilling fluid in an amount equal to from about 50 to about 1000 ppm of said material in said drilling fluid.

8. In workover operations in a well penetrating a subterranean formation wherein a workover fluid containing calcium, magnesium, barium or zinc is used in the presence of carbon dioxide during said workover operations, an improvement comprising:
   (a) maintaining said workover fluid at a pH from about 2 to about 9; and
   (b) adding from about 1 to about 5000 parts per million of a phosphonomethylated oxyalkyleneamine material having a molecular weight from about 150 to about 3000 to said workover fluid, to prevent formation of divalent metal carbonate scale during said workover operations wherein said material consists essentially of from about 2.8 to about 7.0 weight percent sodium phosphonate of monoethanolamine, from about 2.8 to about 7.0 weight percent sodium phosphonate of morpholine, from about 34 to about 85 weight percent sodium phosphonate of bisamine ethyl ether, from about 17 to about 26 weight percent of sodium phosphonate of diglycolamine and from about 3.5 to about 8.7 weight percent sodium phosphonate of N-ethyl diglycolamine.

9. The method of claim 8 wherein said material is added to said workover fluid as an aqueous solution containing from about 20 to about 45 weight percent of said material.

10. The method of claim 8 wherein said material is added to said workover fluid in an amount equal to from about 50 to about 1000 ppm of said material in said workover fluid.

11. In a method for completing a well penetrating a subterranean formation wherein a completion fluid containing calcium, magnesium, barium or zinc is used in the presence of carbon dioxide during completion operations, an improvement comprising:
 (a) maintaining said completion fluid at a pH from about 2 to about 9; and,
 (b) adding from about 1 to about 5000 parts per million of a phosphonomethylated oxyalkyleneamine material having a molecular weight from about 150 to about 3000 to said completion fluid, to prevent formation of divalent metal carbonate scale during said completion operations wherein said material consists essentially of from about 2.8 to about 7.0 weight percent sodium phosphonate of monoethanolamine, from about 2.8 to about 7.0 weight percent sodium phosphonate of morpholine, from about 34 to about 85 weight percent sodium phosphonate of bisamine ethyl ether, from about 17 to about 26 weight percent of sodium phosphonate of diglycolamine and from about 3.5 to about 8.7 weight percent sodium phosphonate of N-ethyl diglycolamine.

12. The method of claim 11 wherein said material is added to said completion fluid as an aqueous solution containing from about 20 to about 45 weight percent of said material.

13. The method of claim 11 wherein said material is added to said completion fluid in an amount equal to from about 50 to about 1000 ppm of said material in said completion fluid.

* * * * *